US008097753B2

(12) United States Patent
Maas et al.

(10) Patent No.: US 8,097,753 B2
(45) Date of Patent: *Jan. 17, 2012

(54) MIXTURES COMPOSED OR MONOCARBOXY-FUNCTIONALIZED DIALKYLPHOSPHINIC ACIDS, THEIR USE AND A PROCESS FOR THEIR PREPARATION

(75) Inventors: Wiebke Maas, Huerth (DE); Werner Krause, Huerth (DE); Harald Bauer, Kerpen (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 11/714,482

(22) Filed: Mar. 6, 2007

(65) Prior Publication Data

US 2007/0213436 A1    Sep. 13, 2007

(30) Foreign Application Priority Data

Mar. 7, 2006    (DE) .................... 10 2006 010 362

(51) Int. Cl.
*C07F 9/22* (2006.01)
(52) U.S. Cl. ....................................... 562/24
(58) Field of Classification Search ................ None
See application file for complete search history.

(56) References Cited

U.S. PATENT DOCUMENTS

| | | | | | |
|---|---|---|---|---|---|
| 2,279,501 | A | * | 4/1942 | Dickey et al. ................. | 428/393 |
| 2,579,810 | A | * | 12/1951 | Fields ........................... | 558/135 |
| 2,957,931 | A | | 10/1960 | Hamilton et al. | |
| 3,021,279 | A | * | 2/1962 | Scanley ........................ | 507/237 |
| 3,178,469 | A | * | 4/1965 | Fields ........................... | 558/129 |
| 3,974,243 | A | * | 8/1976 | Kleiner ......................... | 558/198 |
| 4,018,854 | A | * | 4/1977 | McIntosh ...................... | 558/181 |
| 4,020,101 | A | * | 4/1977 | Geffers et al. ................. | 562/24 |
| 4,088,677 | A | * | 5/1978 | Kleiner ......................... | 562/24 |
| 4,138,433 | A | | 2/1979 | Kleiner et al. | |
| 5,376,731 | A | * | 12/1994 | Kerr et al. ..................... | 525/340 |
| 6,017,903 | A | | 1/2000 | Slusher et al. | |
| 6,090,976 | A | * | 7/2000 | Kim et al. ..................... | 562/24 |
| 6,355,832 | B1 | * | 3/2002 | Weferling et al. .............. | 562/8 |
| 6,534,673 | B1 | * | 3/2003 | Weferling et al. .............. | 562/8 |
| 6,753,363 | B1 | | 6/2004 | Harashina | |
| 7,129,320 | B2 | * | 10/2006 | Sicken et al. .................. | 528/398 |
| 7,148,276 | B2 | * | 12/2006 | Bauer et al. ................... | 524/126 |
| 2005/0101704 | A1 | * | 5/2005 | Eisentraeger et al. ........ | 524/100 |
| 2005/0101706 | A1 | * | 5/2005 | Bauer et al. ................... | 524/115 |
| 2005/0137418 | A1 | * | 6/2005 | Bauer et al. ................... | 562/8 |
| 2005/0143503 | A1 | * | 6/2005 | Bauer et al. ................... | 524/115 |
| 2006/0074157 | A1 | * | 4/2006 | Bauer et al. ................... | 524/115 |
| 2006/0084734 | A1 | * | 4/2006 | Bauer et al. ................... | 524/115 |
| 2006/0214144 | A1 | * | 9/2006 | Bauer et al. ................... | 252/609 |
| 2006/0217469 | A1 | * | 9/2006 | Bauer et al. ................... | 524/115 |
| 2006/0226404 | A1 | * | 10/2006 | Bauer et al. ................... | 252/601 |
| 2006/0287418 | A1 | * | 12/2006 | Bauer et al. ................... | 524/127 |
| 2007/0027297 | A1 | * | 2/2007 | Sicken et al. .................. | 528/398 |
| 2007/0213436 | A1 | * | 9/2007 | Maas et al. .................... | 524/133 |
| 2008/0188598 | A1 | | 8/2008 | Bauer et al. | |

FOREIGN PATENT DOCUMENTS

| | | |
|---|---|---|
| DE | 2528420 | 1/1977 |
| EP | 0063896 | 11/1982 |
| EP | 0266978 | 5/1988 |
| EP | 0516346 | 12/1992 |
| EP | 1544205 | 6/2005 |
| JP | 07197319 | 8/1995 |
| JP | 2000344843 | 12/2001 |
| WO | WO 98/53812 | 12/1998 |

OTHER PUBLICATIONS

Abstract and computer generated translation of JP 05-247068, published Sep. 1993.*
6,248,921, Jun. 19, 2001, Weferling et al.
Co-pending U.S. Appl. No. 11/714,481 by Maas et al., filed Mar. 6, 2007.
Co-pending U.S. Appl. No. 11/714,331 by Maas et al., filed Mar. 6, 2007.
German Search Report for DE 102006010362.9, Oct. 24, 2006.
English abstract for JP 07102418, Apr. 18, 1995.
Sasse, "Phosphinsauren und deren Derivate," Houben-Weyl vol. 12/1, p. 230 (1963).
V.K. Khajrullin et al., "Reactions of Methylphosphonous Dichloride with Methacrylic and Propiolic Acids," obsc. Chim. 38 pp. 291-294 (1968).
English Abstract of JP 05194562, Aug. 3, 1993.
Sasse, "Phosphonigo Sauren und deren Derivato" Houben-Weyl, vol. 12/1, p. 306 (1963). Kurdyumova et al., "Synthesis of Phosphinic Acids from Hypophosphites. I. Acrylates as an Unsaturated component," Russian Journal of General Chemistry, vol. 67 No. 12 (English Translation) pp. 1852-1856 (1997).
Krairullin et al., Z. Obschei. Khim. pp. 289-296 (1966).
EPO Search Report for EPO7004222, Jul. 5, 2007.
Khairullin, V.K. et al. "Reaction of Chlorides of Acids of Trivalent Phosphorus with Conjugated Systems. I. Reaction of Ethylphosphonous dichloride with alpha, beta—unsaturated Acids," Zhurnal Obshchei Khimii, 36(2), pp. 289-296, XP008078816 (1966).

(Continued)

*Primary Examiner* — Rosalynd Keys
(74) *Attorney, Agent, or Firm* — Anthony A. Bisulca

(57) ABSTRACT

The invention relates to mixtures composed of monocarboxy-functionalized dialkylphosphinic acids and of further components, which comprise
A) from 98 to 100% by weight of monocarboxy-functionalized dialkylphosphinic acids of the formula (I)

$$\begin{array}{c} R_3 \quad R_6 \quad O \\ | \quad O \quad | \quad \| \\ R_2-\overset{|}{\underset{R_1}{C}}-\overset{\|}{\underset{OX}{P}}-\overset{|}{\underset{R_7}{C}}-OY \\ R_4 \quad R_5 \end{array} \quad (I)$$

in which $R_1$, $R_2$, $R_3$, $R_4$, $R_5$, $R_6$, and $R_7$ are identical or different and, independently of one another, are H, methyl, ethyl, n-propyl, isopropyl, n-butyl, isobutyl, tert-butyl, and/or phenyl,
X and Y are identical or different and, independently of one another, are H, Li, Na, K, or $NH_4$, and
B) from 0 to 2% by weight of halogens,
where the entirety of the components always amounts to 100% by weight.

8 Claims, No Drawings

OTHER PUBLICATIONS

Khairullin, V.K. et al. "Reaction of Sthylphosphonous Dichloride with Crotonic Acid," Zhurnal Obshchei Khimii 35(3), pp. 494-498; XP00908084872 (1966).

Pudouik, a.n. et al., "New Method of Synthesis of Esters of Phosphonic and Thiophosphonic Acids. IVI Synthesis of Esters of mono-and diphosphono—and thiophosphonocarboxylic Acids," Izzestiya Akademii Nauk SSSR, Seriya Khimiches Khimicheskaya, pp. 636-645, XP009084884 (1954).

Grobelny D. et al., "Binding Energetics of Phosphorus—Containing Inhibitors of Thermolysin" Biochemistry, American Chemical Society Bd. 28, Nr. 12, pp. 4948-4951 (Jun. 1, 1989).

EPO Search Report for EP 07023436 which corresponds to document AA above, mailed Mar. 6, 2008.

* cited by examiner

MIXTURES COMPOSED OR MONOCARBOXY-FUNCTIONALIZED DIALKYLPHOSPHINIC ACIDS, THEIR USE AND A PROCESS FOR THEIR PREPARATION

The present invention is described in the German priority application No. 10 2006 010 362.9, filed Jul. 3, 2006, which is hereby incorporated by reference as is fully disclosed herein.

The invention relates to mixtures composed of monocarboxy-functionalized dialkylphosphinic acids, to their use, and to a process for their preparation.

Many monocarboxy-functionalized dialkylphosphinic acids and derivatives of these are known; they are mainly used as flame retardants. Various processes can be used for their preparation.

The prior art contains many descriptions of processes in which a monocarboxy-functionalized dialkylphosphinic acid or its anhydride is obtained by reacting phosphonous dihalides (dihalophosphines) with activated olefinic compounds, e.g. acrylic acid derivatives or methacrylic acid derivatives (Houben-Weyl, volume 12/1, p. 230; V. K. Khajrullin, F. M. Kondrat'eva and A. N. Pudovik, Z. obsc. Chim. 38, 291-294 (1968); DE-A-2 528 420, JP-A-05/194 562).

A disadvantage of the abovementioned prior art is formation of halogen-containing by-products resulting from the synthesis. Halogen-containing compounds here are chemical compounds in which atoms of the 7$^{th}$ main group are present, in particular fluorine, chlorine, bromine, and iodine, chemically bonded to carbon or phosphorus. Other halogen-containing compounds are salts which contain halide anions. Halogen-containing compounds, in particular chlorine-containing compounds, are often many times more corrosive than halogen-free compounds.

A disadvantage of halogen-containing compounds in relation to use as flame retardants is that corrosive and toxic gases can form in the event of a fire, and these make the use of compounds of this type as flame retardants at least questionable, or indeed entirely impossible. Among the phosphonic dihalides most frequently used is methyldichlorophosphine, which in turn has hitherto been prepared by a very complicated synthesis from phosphorus trichloride and methyl chloride in the presence of aluminum chloride (Houben-Weyl, volume 12/1, p. 306). The reaction is highly exothermic and is difficult to control under industrial conditions. Furthermore, various by-products, in particular halogen-containing by-products, are formed, and these, like some of the abovementioned starting materials themselves, are toxic and/or corrosive, i.e. highly undesirable. The use of these starting materials and the by-products obtained therefrom is undesirable in view of corrosion and environmental incompatibility.

Another method for synthesis of monocarboxy-functionalized dialkylphosphinic acids is based on the reaction of bis(trimethylsilyl)phosphonite, HP(OSiMe$_3$)$_2$, with (α,β-unsaturated carboxylic acid components, subsequent alkylation with alkyl halides by the Arbuzov reaction, and alcoholysis to give the corresponding dialkylphosphinic acid (Kurdyumova, N. R.; Rozhko, L. F.; Ragulin, V. V.; Tsvetkov, E. N.; Russian Journal of General Chemistry (Translation of Zhurnal Obshchei Khimii) (1997), 67(12), 1852-1856).

This synthesis route too, has the disadvantage of requiring the use of halogen-containing compounds.

The bis(trimethylsilyl)phosphonite used as starting material here is obtained from potassium hypophosphite or from ammonium hypophosphite via reaction with hexamethyldisilazane.

Hexamethyldisilazane is not available in industrial quantities, and its use is not cost-effective, since its preparation is likewise complicated. This route cannot be used for economic and cost-effective preparation of monocarboxy-functionalized dialkylphosphinic acids.

EP-0 516 346 A1 describes the preparation of phosphinic acid telomers via reaction of sodium hypophosphite with acrylic acid components in the presence of a free-radical initiator. The acrylic acid component is used in excess in order to form telomers. The telomers can be used as scale inhibitors.

There is therefore a need for monocarboxy-functionalized dialkylphosphinic acids which have low halogen content or indeed are halogen-free.

There is also a need for a process for preparation of monocarboxy-functionalized dialkylphosphinic acids which can be carried out in a simple and cost-effective manner with little or no use of halogen and which gives unitary products in high yield and purity. This process should also be markedly superior to those known hitherto in terms of environmental technology.

Another object of the invention is therefore to provide a process which can prepare monocarboxy-functionalized dialkylphosphinic acids and which avoids the abovementioned disadvantages of the prior art, and which starts from hypophosphorous acid or from its salts.

However, a first object of the present invention is to provide monocarboxy-functionalized dialkylphosphinic acids which have extremely low halogen content or are halogen-free.

This object is achieved via mixtures composed of dialkylphosphinic acids and of further components, which comprise A) from 98 to 100% by weight of monocarboxy-functionalized dialkylphosphinic acids of the formula (I)

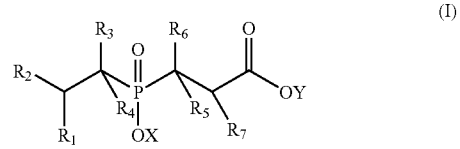

in which R$_1$, R$_2$, R$_3$, R$_4$, R$_5$, R$_6$, and R$_7$ are identical or different and, independently of one another, are H, methyl, ethyl, n-propyl, isopropyl, n-butyl, isobutyl, tert-butyl, and/or phenyl, X and Y are identical or different and, independently of one another, are H, Li, Na, K, or NH$_4$, and B) from 0 to 2% by weight of halogens, where the entirety of the components always amounts to 100% by weight.

The mixtures preferably comprise from 99.9995 to 100% by weight of monocarboxy-functionalized dialkylphosphinic acids of the formula (I) and from 0 to 0.0005% by weight of halogens.

The monocarboxy-functionalized dialkylphosphinic acid is preferably 3-(ethylhydroxyphosphinyl)propionic acid, 3-(propylhydroxyphosphinyl)propionic acid, 3-(ethyl-hydroxyphosphinyl)butyric acid, 3-(ethylhydroxyphosphinyl)-2-methylpropionic acid, 3-(butylhydroxyphosphinyl)propionic acid, 3-(propylhydroxyphosphinyl)butyric acid, 3-(butylhydroxyphosphinyl)butyric acid, 3-(ethylhydroxyphosphinyl)pentanoic acid, 3-(propylhydroxyphosphinyl)pentanoic acid, 3-(butylhydroxyphosphinyl)pentanoic acid, 3-(propylhydroxyphosphinyl)-2-methylpropionic acid, 3-(butylhydroxyphosphinyl)-2-methylpropionic acid, 3-(ethylhydroxyphosphinyl)-2-methylbutyric acid, 3-(propyl-hydroxyphosphinyl)-2-methylbutyric acid, and/or 3-(butylhydroxyphosphinyl)-2-methylbutyric acid.

The object is also achieved via a process for preparation of mixtures as claimed in one or more of claims 1 to 3, which comprises reacting hypophosphorous acid or its salts (component C) of the formula II

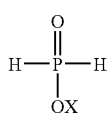

in which X is H, Na, K, or $NH_4$ in the presence of a free-radical initiator with an $\alpha,\beta$-unsaturated carboxylic acid derivative (component D) of the formula III,

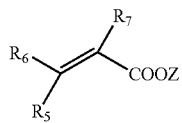

in which $R_5$, $R_6$, and $R_7$ are defined as in formula I, and Z is H, $C_{1-18}$-alkyl, or $C_{6-18}$-aryl, or is Y, and with an olefin (component E) of the formula IV

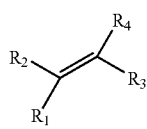

in which $R_1$, $R_2$, $R_3$, and $R_4$ are defined as in formula I.

It is preferable that $R_1$, $R_2$, $R_3$, $R_4$, $R_5$, $R_6$, and $R_7$ are identical or different and, independently of one another, are H, methyl, ethyl, n-propyl, isopropyl, n-butyl, isobutyl, tert-butyl, and/or phenyl.

It is preferable that X is H and Z is H, methyl, ethyl, n-propyl, isopropyl, n-butyl, isobutyl, tert-butyl, hydroxyethyl, or hydroxypropyl.

The object is also achieved via a process in which, in a step 1, component C is reacted in the presence of a free-radical initiator with component E to give an alkylphosphonous acid and, in step 2, the resultant reaction solution is esterified with an alcohol and phosphonous ester produced here is removed by distillation and then, in a step 3, is reacted in the presence of a free-radical initiator or of a basic initiator with component D, and then the resultant reaction solution here is hydrolyzed, in a step 4, with acidic catalysis, in order to obtain component A (monocarboxy-functionalized dialkylphosphinic acid).

It is preferable that, in step 2, the alkylphosphonous acid is directly esterified with a linear or branched alcohol of the formula M-OH, where M is a linear or branched alkyl radical having from 1 to 10 carbon atoms.

It is preferable that the alcohol is n-butanol, isobutanol or ethylhexanol.

It is preferable that component C is the ammonium or sodium salt of hypophosphorous acid.

It is preferable that the initiator is a free-radical, anionic, cationic, or photochemical initiator.

It is preferable that the initiator is peroxide-forming compounds and/or peroxo compounds, e.g. hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-tert-butyl peroxide, and/or peroxodisulfuric acid, and/or is azo compounds, e.g. azodiisobutyronitrile, 2,2-azobis(2-amidinopropane)dihydrochloride and/or 2,2'-azobis (N,N'-dimethyleneisobutyramidine)dihydrochloride.

It is preferable that the $\alpha,\beta$-unsaturated carboxylic acids are acrylic acid, methyl acrylate, ethyl acrylate, methacrylic acid, hydroxyethyl acrylate, crotonic acid, ethyl crotonate and/or tiglic acid (trans-2,3-dimethylacrylic acid).

It is preferable that the olefin is ethylene, propylene, n-butene, and/or isobutene, or any desired mixture thereof, 1-hexene, 1-heptene, and/or 1-octene; allyl alcohol, allylamine, allylbenzene, allylanisole, styrene, $\alpha$-methylstyrene, 4-methylstyrene, and/or vinyl acetate.

It is preferable that the reaction of component C with components D and/or E takes place at a temperature of from 50 to 150° C.

A further process for preparation of the inventive mixtures comprises reacting component C, in a step 1, with a ketone to give 1-hydroxy-1-dialkylphosphinate, reacting this 1-hydroxy-1-dialkylphosphinate, in a step 2, in the presence of a free-radical initiator with component D, then, in a step 3, removing the ketone, and reacting the resultant reaction mixture, in a step 4, in the presence of a free-radical initiator with component E.

Another process for preparation of the inventive mixtures comprises reacting component C, in a step 1, with a ketone to give 1-hydroxy-1-dialkylphosphinate, reacting this 1-hydroxy-1-dialkylphosphinate, in a step 2, in the presence of a free-radical initiator with component E, then, in a step 3, removing the ketone, and reacting the resultant reaction mixture, in a step 4, in the presence of a free-radical initiator with component D.

A further process for preparation of the mixtures as claimed in one or more of claims 1 to 3 comprises reacting component C, in a step 1, with acetone to give 1-hydroxy-1-methylethylphosphinate, reacting this 1-hydroxy-1-methylethylphosphinate, in a step 2, in the presence of a free-radical initiator with component E, then, in a step 3, removing the acetone, and reacting the resultant reaction mixture, in a step 4, in the presence of a free-radical initiator with component D.

It is preferable that, with the use of component D, where $Z=C_{1-18}$-alkyl or $C_{6-18}$-aryl, the monocarboxy-functionalized dialkylphosphinic ester formed is hydrolyzed.

The invention also provides the use of mixtures as claimed in one or more of claims 1 to 3 as flame retardant or for preparation of flame retardants.

The mixtures are preferably used as flame retardants or for preparation of flame retardants, of flame-retardant molding compositions, and/or of flame-retardant moldings, of flame-retardant films, of flame-retardant filaments, and of flame-retardant fibers.

It is preferable that the flame-retardant molding composition and, respectively, the moldings, films, filaments, and fibers comprise from 1 to 50% by weight of the mixtures as claimed in one or more of claims 1 to 3, from 1 to 99% by weight of polymer or a mixture of the same, from 0 to 60% by weight of additives, and from 0 to 60% by weight of filler, where the entirety of the components always amounts to 100% by weight.

In principle, the groups $R_1$, $R_2$, $R_3$, $R_4$, $R_5$, $R_6$, and $R_7$ in formula 1 can be identical or different and are independently of one another, $C_1$-$C_{18}$-alkyl, $C_6$-$C_{18}$-aryl, $C_6$-$C_{18}$-aralkyl, $C_6$-$C_{18}$-alkylaryl, CN, CHO, OC(O)CH$_2$CN, CH(OH)C$_2$H$_5$, CH$_2$CH(OH)CH$_3$, 9-anthracene, 2-pyrrolidone, (CH$_2$)$_m$OH, (CH$_2$)$_m$NH$_2$, (CH$_2$)$_m$NCS, (CH$_2$)$_m$NC(S)NH$_2$, (CH$_2$)$_m$SH, (CH$_2$)$_m$S-2-thiazoline, (CH$_2$)$_m$SiMe$_3$, C(O)R$_8$, (CH$_2$)$_m$C(O)R$_8$, CH=CH—R$_8$, CH=CH—C(O)R$_8$, where R$_8$ is $C_1$-$C_8$-alkyl or $C_6$-$C_{18}$-aryl, and m is a whole number from 0 to 10, preferably from 1 to 10.

These mixtures preferably comprise from 99 to 100% by weight of dialkylphosphinic acids of the formula (I) and from 0 to 1% by weight of halogen.

These mixtures particularly preferably comprise from 99.99 to 100% by weight of dialkylphosphinic acids of the formula (I) and from 0 to 0.01% by weight of halogens.

The mixtures in particular comprise from 99.9995 to 100% by weight of monocarboxy-functionalized dialkylphosphinic acids of the formula (I) and from 0 to 0.0005% by weight of halogens.

It is preferable that the groups $C_6$-$C_{18}$-aryl, $C_6$-$C_{18}$-aralkyl and $C_6$-$C_{18}$-alkylaryl have substitution by SO$_3$X$_2$, —C(O)CH3, OH, CH$_2$OH, CH$_3$SO$_3$X$_2$, PO$_3$X$_2$, NH$_2$, NO$_2$, OCH$_3$, SH, and/or OC(O)CH$_3$.

The mixtures preferably comprise

A) from 99.9995 to 100% by weight of 3-(ethylhydroxyphosphinyl)propionic acid, 3-(propylhydroxyphosphinyl)propionic acid, 3-(ethylhydroxyphosphinyl)butyric acid, 3-(ethylhydroxyphosphinyl)-2-methylpropionic acid, 3-(butylhydroxyphosphinyl)-propionic acid, 3-(propylhydroxyphosphinyl)butyric acid, 3-(butylhydroxyphosphinyl)butyric acid, 3-(ethylhydroxyphosphinyl)pentanoic acid, 3-(propylhydroxyphosphinyl)pentanoic acid, 3-(butylhydroxyphosphinyl)pentanoic acid, 3-(propylhydroxyphosphinyl)-2-methylpropionic acid, 3-(butylhydroxyphosphinyl)-2-methylpropionic acid, 3-(ethylhydroxyphosphinyl)-2-methylbutyric acid, 3-(propylhydroxyphosphinyl)-2-methylbutyric acid, and/or 3-(butylhydroxyphosphinyl)-2-methylbutyric acid, and B) from 0 to 0.0005% by weight of chlorine.

The conduct of the process is preferably such that, in a first step of the process, component C is reacted in the presence of a free-radical initiator with component D, and in a second step of the process the resultant reaction solution is reacted likewise in the presence of a free-radical initiator with component E.

In another procedure, in a first step of the process, component C is reacted in the presence of a free-radical initiator with component E and, in a second step of the process, the resultant reaction solution is reacted likewise in the presence of a free-radical initiator with component D.

The inventive process moreover comprises use of the following molar ratios of components C, D, and E:

$$pC + \sum_{k=1}^{n-1} x_k D + \sum_{k=1}^{n-1} y_k E + (\alpha - x_n)D + (\alpha - y_n)E = A$$

where C is hypophosphorous acid or its salts of the formula II, D is the α,β-unsaturated carboxylic acid derivative of the formula III, E is the olefin of the formula IV, and A is the monocarboxy-functionalized dialkylphosphinic acid of the formula I, and moreover:

$$\sum_{k=1}^{n} x_k = \alpha \text{ and } \sum_{k=1}^{n} y_k = \alpha,$$

where α=from 1 to 3; 0.01≦$x_k$ and $y_k$≦α; p=from 0.5 to 3, and n=from 1 to 100.

The conduct of the process can also be such that, in a first step 1, component C is reacted in the presence of a free-radical initiator with a portion $x_k$ D of component D, the resultant reaction solution is reacted, in a step 2, in the presence of a free-radical initiator with the entire amount of component E, and the resultant reaction solution is reacted, in a step 3, in the presence of a free-radical initiator with the remaining portion (α-$x_n$) D of component D.

The conduct of the process can moreover also be such that, in a first step 1, component C is reacted in the presence of a free-radical initiator with a portion $y_k$ E of component E, the resultant reaction solution is reacted, in a step 2, in the presence of a free-radical initiator with the entire amount of component D, and the resultant reaction solution is reacted, in a step 3, in the presence of a free-radical initiator with the remaining portion (α-$y_n$) E of component E.

The conduct of the process can moreover also be such that, in a step 1, component C is reacted in the presence of a free-radical initiator with a portion $x_k$ D of component D, and the resultant reaction solution is reacted, in a step 2, in the presence of a free-radical initiator with a portion $y_k$ E of component E, where steps 1 and 2 are alternated sufficiently often to consume the respective portions.

The conduct of the process can moreover also be such that, in a step 1, component C is reacted in the presence of a free-radical initiator with a portion $y_k$ E of component E, and the resultant reaction solution is reacted, in a step 2, in the presence of a free-radical initiator with a portion $x_k$ D of component D, where steps 1 and 2 are alternated sufficiently often to consume the respective portions.

The conduct of the process can also be varied in such a way that, in a step 1, component C is reacted in the presence of a free-radical initiator with component E to give an alkylphosphonous acid and, in step 2, the resultant reaction solution is esterified with an alcohol and phosphonous ester produced here is removed by distillation and then, in a step 3, is reacted in the presence of a free-radical initiator or of a basic initiator with component D, and then the resultant reaction solution here is hydrolyzed, in a step 4, with acidic catalysis, in order to obtain component A (monocarboxy-functionalized dialkylphosphinic acid).

It is preferable that the amounts used of the free-radical initiator are from 0.001 to 10 mol %, based on the phosphorus-containing compound.

It is preferable that the rate of feed of the free-radical initiator is from 0.01 to 10 mol % of initiator per hour, based on the phosphorus-containing compound.

It is preferable that the ratio of olefin to hypophosphite and/or hypophosphorous acid (on a molar basis) is from 1:3 to 3:0.5, in particular from 1.5:3 to 2.5:1.

It is preferable that the reaction with the olefin component E takes place at a pressure of the olefin used of from 1 to 100 bar, in particular from 1 to 50 bar.

It is preferable that the reaction of component C with components D and/or E takes place at a temperature of from 0 to 250° C., in particular at from 20 to 200° C.

It is preferable that the reaction of component C with components D and/or E takes place at a temperature of from 50 to 150° C.

A further process for preparation of mixtures as claimed in one or more of claims 1 to 3 comprises reacting component C, in a step 1, with a ketone to give 1-hydroxy-1-dialkylphosphinate, reacting this 1-hydroxy-1-dialkylphosphinate, in a step 2, in the presence of a free-radical initiator with component D, then, in a step 3, removing the ketone, and reacting the resultant reaction mixture, in a step 4, in the presence of a free-radical initiator with component E.

The conduct of the abovementioned process can also be such that component C, in a step 1, is reacted with a ketone to give 1-hydroxy-1-dialkylphosphinate, reacting this 1-hydroxy-1-dialkylphosphinate, in a step 2, in the presence of a free-radical initiator with component E, then, in a step 3, removing the ketone, and reacting the resultant reaction mixture, in a step 4, in the presence of a free-radical initiator with component D.

It is preferable that the flame retardant comprises from 0.1 to 90% by weight of the mixtures as claimed in one or more of claims 1 to 3 and from 0.1 to 50% by weight of further additives, where the entirety of the components always amounts to 100% by weight.

It is particularly preferable that the flame retardant comprises from 10 to 80% by weight of the mixtures as claimed in one or more of claims 1 to 3 and from 10 to 40% by weight of further additives, where the entirety of the components always amounts to 100% by weight.

It is preferable that the mixtures as claimed in one or more of claims 1 to 3 are used in flame-retardant molding compositions.

It is particularly preferably that the flame-retardant molding composition comprises from 5 to 30% by weight of the mixtures as claimed in one or more of claims 1 to 3, from 5 to 90% by weight of polymer or a mixture of the same, from 5 to 40% by weight of additives, and from 5 to 40% by weight of filler, where the entirety of the components always amounts to 100% by weight.

Finally, the invention also relates to the use of mixtures as claimed in one or more of claims 1 to 3 as flame retardant in flame-retardant moldings in flame-retardant films, in flame-retardant filaments, and in flame-retardant fibers.

It is particularly preferable that the moldings, films, filaments, and fibers comprise from 5 to 30% by weight of the mixtures as claimed in one or more of claims 1 to 3, from 5 to 90% by weight of polymer or a mixture of the same, from 5 to 40% by weight of additives, and from 5 to 40% by weight of filler, where the entirety of the components always amounts to 100% by weight.

The additives are preferably antioxidants, antistatic agents, blowing agents, further flame retardants, heat stabilizers, impact modifiers, processing auxiliaries, lubricants, light stabilizers, antidrip agents, compatibilizers, reinforcing materials, nucleating agents, additives for laser marking, hydrolysis stabilizers, chain extenders, color pigments, and/or plasticizers.

The term "halogens" is defined as including not only the pure halogens, such as fluorine, chlorine, bromine, and iodine, but also halogen-containing compounds which may be of either inorganic or organic type.

The inventive mixtures are in particular free from the halogen-containing compounds which occur in the synthesis processes of the prior art and of which only limited amounts can then be removed from the desired product, the consequence being that these products always have an undesired content of halogen or of halogen-containing compounds—even if this is sometimes very small.

The degree of freedom from halogen of the inventive mixtures has not previously been achieved and can be so low as to be at the theoretical limit of detection. In particular, it is possible to minimize chlorine content.

The inventive mixtures preferably comprise

A) from 99.9995 to 100% by weight of 3-(ethylhydroxyphosphinyl)propionic acid, 3-(propylhydroxyphosphinyl)propionic acid, 3-(butylhydroxyphosphinyl)propionic acid, 3-(isobutylhydroxyphosphinyl)propionic acid, 3-(pentylhydroxyphosphinyl)propionic acid, 3-(hexylhydroxyphosphinyl)propionic acid, 3-(hydroxyethylhydroxyphosphinyl)propionic acid, 3-(ethylbenzylhydroxyphosphinyl)propionic acid, 3-(ethylhydroxyphosphinyl)butyric acid, 3-(propylhydroxyphosphinyl)butyric acid, 3-(butylhydroxyphosphinyl)butyric acid, 3-(isobutylhydroxyphosphinyl)butyric acid, 3-(pentylhydroxyphosphinyl)butyric acid, 3-(hexylhydroxyphosphinyl)butyric acid, 3-(hydroxyethylhydroxyphosphinyl)butyric acid, 3-(ethylbenzylhydroxyphosphinyl)butyric acid, 3-(ethylhydroxyphosphinyl)pentanoic acid, 3-(propylhydroxyphosphinyl)pentanoic acid, 3-(butylhydroxyphosphinyl)pentanoic acid, 3-(isobutylhydroxyphosphinyl)pentanoic acid, 3-(pentylhydroxyphosphinyl)pentanoic acid, 3-(hexylhydroxyphosphinyl)-pentanoic acid, 3-(hydroxyethylhydroxyphosphinyl)pentanoic acid, 3-(ethylbenzylhydroxyphosphinyl)pentanoic acid, 3-(ethylhydroxyphosphinyl)-2-methylpropionic acid, 3-(propylhydroxyphosphinyl)-2-methylpropionic acid, 3-(butylhydroxyphosphinyl)-2-methylpropionic acid, 3-(isobutylhydroxyphosphinyl)-2-methylpropionic acid, 3-(pentylhydroxyphosphinyl)-2-methylpropionic acid, 3-(hexylhydroxyphosphinyl)-2-methylpropionic acid, 3-(hydroxyethylhydroxyphosphinyl)-2-methylpropionic acid, 3-(ethylbenzylhydroxyphosphinyl)-2-methylpropionic acid, 3-(ethylhydroxyphosphinyl)-2-methylbutyric acid, 3-(propylhydroxyphosphinyl)-2-methylbutyric acid, 3-(butylhydroxyphosphinyl)-2-methylbutyric acid, 3-(isobutylhydroxyphosphinyl)-2-methylbutyric acid, 3-(pentylhydroxyphosphinyl)-2-methylbutyric acid, 3-(hexylhydroxyphosphinyl)-2-methylbutyric acid, 3-(hydroxyethylhydroxyphosphinyl)-2-methylbutyric acid, and/or 3-(ethylbenzylhydroxyphosphinyl)-2-methylbutyric acid, and B) from 0 to 0.0005% by weight of chlorine.

These abovementioned mixtures are preferably prepared by the inventive process.

The inventive process has considerable advantages over the prior art, since it entirely avoids phosphonous dihalides and other halogen-containing compounds. With this, the inventive products, the monocarboxy-functionalized dialkylphosphinic acids, are also less corrosive than the monocarboxy-functionalized dialkylphosphinic acids obtainable hitherto. The lower corrosivity is advantageous not only for handling during the preparation process but also during use as flame retardant.

The conduct of the inventive process is such that component C is reacted in the presence of a free-radical initiator with component D and E in a solvent, components D and E being respectively fed separately (in series or in sequence) rather than simultaneously.

If the component D used is not a free carboxylic acid but a carboxylic ester, hydrolysis has to be carried out prior to or after the reaction described, in order to obtain the free carboxylic acid.

Surprisingly, the monocarboxy-functionalized dialkylphosphinic acid can be obtained in good yields via iterative reaction of α,β-unsaturated carboxylic acids or α,β-unsaturated carboxylic esters and olefins with derivatives of hypophosphorous acid without isolation of the respective monoalkylphosphinic acid derivative. Reaction with an α,β-unsaturated carboxylic ester also requires a hydrolysis step, in order to obtain the free monocarboxy-functionalized dialkylphosphinic acid.

It is preferable that in step b) the ester of the alkylphosphonous acid is removed by distillation.

Esterification of the phosphonous acid to give the corresponding monoester can, for example, be achieved via reaction with relatively high-boiling-point alcohols, while using azeotropic distillation to remove the water formed.

The addition reaction in step c) preferably takes place in the presence of catalysts.

It is preferable that these are basic catalysts. As an alternative, it is also possible to use free-radical initiators or cationic initiators.

It is preferable that the basic initiators are alkali metal alcoholates and/or alkaline earth metal alcoholates. It is particularly preferably that sodium methanolate or sodium ethanolate is used.

It is preferable that the hydrolysis of the ester takes place in the presence of a strong mineral acid. It is preferable that this is concentrated sulfuric acid.

It is preferable that the ratio of α,β-unsaturated carboxylic acid derivatives and olefins to hypophosphite and/or hypophosphorous acid (on a molar basis) in accordance with the abovementioned formula is:

$0.01 \leq x_k$ and $y_k \leq \alpha, \alpha=1-3, p=0.5-3.0,$ and $n=1-100,$ preferably $0.05 \leq x_k$ and $y_k \leq \alpha, \alpha=1-1.5, p=0.8-1.2, n=2-20.$ It is preferable that inorganic solvents, organic solvents, or any desired mixture of the same are used, the preferred inorganic solvent being water.

It is preferable that the pH is adjusted to from 0 to 14 in the case of aqueous solvent, particularly preferably from 2 to 9.

It is preferable that the pH is adjusted using mineral acids, acidic salts, carboxylic acids, alkalis and/or electrolytes, e.g. sodium bisulfate, sodium bisulfite, and/or potassium bisulfite.

It is preferable that the carboxylic acids are formic acid, acetic acid, propionic acid, butyric acid, and/or relatively-long-chain carboxylic acids, and/or their dimers, oligomers, and/or polymers.

It is preferable that the salt of hypophosphorous acid is a salt whose cation is an element of the $1^{st}$ main group and/or whose cation is based on an organically substituted element of the $5^{th}$ main group. It is particularly preferable that it is an ammonium salt or an alkali metal salt, in particular the sodium salt.

It is preferable that the hypophosphorous acid is prepared in situ from salts of hypophosphorous acid and from at least one mineral acid, the ratio of additive acid to hypophosphite (based on equivalents) being from 0:1 to 2:1.

It is preferable that the reaction is carried out in the presence of a free-radical initiator. In principle, suitable free-radical initiators are any of the systems which generate free radicals. The addition reaction of the olefin can be initiated via an anionic initiator or free-radical initiator, or photochemically.

Particularly preferred free-radical initiators are peroxo compounds, such as peroxomonosulfuric acid, potassium persulfate (potassium peroxomonosulfate), caroate, oxones, peroxodisulfuric acid, potassium persulfate (potassium peroxodisulfate), sodium persulfate (sodium peroxodisulfate), ammonium persulfate (ammonium peroxodisulfate).

Particular preference is given to compounds which can form peroxides in the solvent system, e.g. sodium peroxide, sodium peroxide diperoxohydrate, sodium peroxide diperoxohydrate hydrate, sodium peroxide dihydrate, sodium peroxide octahydrate, lithium peroxide, lithium peroxide monoperoxohydrate trihydrate, calcium peroxide, strontium peroxide, barium peroxide, magnesium peroxide, zinc peroxide, potassium hyperoxide, potassium peroxide diperoxohydrate, sodium peroxoborate tetrahydrate, sodium peroxoborate trihydrate, sodium peroxoborate monohydrate, anhydrous sodium peroxoborate, potassium peroxoborate peroxohydrate, magnesium peroxoborate, calcium peroxoborate, barium peroxoborate, strontium peroxoborate, potassium peroxoborate, peroxomonophosphoric acid, peroxodiphosphoric acid, potassium peroxodiphosphate, ammonium peroxodiphosphate, potassium ammonium peroxodiphosphates (double salt), sodium carbonate peroxohydrate, urea peroxohydrate, ammonium oxalate peroxide, barium peroxide peroxohydrate, calcium hydrogen peroxides, calcium peroxide peroxohydrate, ammonium triphosphate diperoxophosphate hydrate, potassium fluoride peroxohydrate, potassium fluoride triperoxohydrate, potassium fluoride diperoxohydrate, sodium pyrophosphate diperoxohydrate, sodium pyrophosphate diperoxohydrate octahydrate, potassium acetate peroxohydrate, sodium phosphate peroxohydrate, sodium silicate peroxohydrate.

Particular preference is given to hydrogen peroxide, performic acid, peracetic acid, benzoyl peroxide, di-tert-butyl peroxide, dicumyl peroxide, 2,4-dichlorobenzoyl peroxide, decanoyl peroxide, lauroyl peroxide, cumene hydroperoxide, pinene hydroperoxide, p-menthane hydroperoxide, tert-butyl hydroperoxide, acetylacetone peroxide, methyl ethyl ketone peroxide, succinic acid peroxide, dicetyl peroxydicarbonate, tert-butyl peroxyacetate, tert-butyl peroxymaleate, tert-butyl peroxybenzoate, acetylcyclohexylsulfonyl peroxide.

It is preferable that water-soluble azo compounds are used as free-radical initiator.

Particular preference is given to azo initiators such as ®VAZO 52, ®VAZO 64 (AIBN), ®VAZO 67, ®VAZO 88, ®VAZO 68 from Dupont-Biesteritz, V-70 2,2'-azobis(4-methoxy-2,4-dimethylvaleronitrile), V-65 2,2'-azobis(2,4-dimethylvaleronitrile), V-601 dimethyl 2,2'-azobis(2-methylpropionate), V-59 2,2'-azobis(2-methylbutyronitrile), V-40, VF-096 1,1'-azobis(cyclohexane-1-carbonitrile), V-30 1-[(cyano-1-methylethyl)azo]formamide, VAm-110 2,2'-azobis(N-butyl-2-methylpropionamide), VAm-111 2,2'-azobis(N-cyclohexyl-2-methylpropionamide), VA-046B 2,2'-azobis[2-(2-imidazolin-2-yl)propane disulfate dihydrate, VA-057 2,2'-azobis[N-(2-carboxyethyl)-2-methylpropionamidine]tetrahydrate, VA-061 2,2'-azobis[2-(2-imidazolin-2-yl)propane], VA-080 2,2'-azobis{2-methyl-N-[1,1-bis(hydroxymethyl)-2-hydroxyethyl]propionamide}, VA-085 2,2'-azobis{2-methyl-N-[2-(1-hydroxybutyl)]propionamide},
VA-086 2,2'-azobis[2-methyl-N-(2-hydroxyethyl)propionamide] from Wako Chemicals.

Preference is also given to azo initiators such as 2-tert-butylazo-2-dimethyl azodiisobutyrate, azodiisobutyronitrile, 2-tert-butylazo-1-cyanocyclohexane, 1-tert-amylazo-1-cyanocyclohexane. Preference is moreover given to alkyl perketals such as 2,2-bis(tert-butylperoxy)butane, ethyl-3,3-bis(tert-butylperoxy)butyrate, 1,1-di-(tert-butylperoxy) cyclohexane.

It is preferable that the free-radical initiator is used in the solvent mentioned. It is also preferable that cyclic olefins are used, e.g. cyclopentene, cyclohexene, cyclohexenols, cyclohexenones, cycloheptene, cyclooctene, cyclooctenols, or cyclooctenones.

It is preferable that functinalized olefins are used, e.g. allyl isothiocyanate, allyl methacrylate, 2-allylphenol, N-allylthiourea, 2-(allylthio)-2-thiazoline, allyltrimethylsilane, allyl acetate, allyl acetoacetate, allyl alcohol, allylamine, allylbenzene, allyl cyanide, allyl cyanoacetate, allylanisole, trans-2-pentenal, cis-2-pentenonitrile, 1-penten-3-ol, 4-penten-1-ol, 4-penten-2-ol, trans-2-hexenal, trans-2-hexen-1-ol, cis-3-hexen-1-ol, 5-hexen-1-ol, styrene, a-methylstyrene, 4-methylstyrene, vinyl acetate, 9-vinyl anthracene, 2-vinylpyridine, 4-vinylpyridine, and 1-vinyl-2-pyrrolidone.

It is preferable that during the reaction with the α,β-unsaturated carboxylic acid the atmosphere is composed of from 50 to 99.9% by weight, preferably from 70 to 95% by weight, of constituents of the solvent and α,β-unsaturated carboxylic acid.

It is preferable that during the reaction with the olefin the atmosphere is composed of from 50 to 99.9% by weight, preferably from 70 to 95% by weight, of constituents of the solvent and olefin.

The atmosphere preferably comprises gaseous components which do not participate in the reaction. The gaseous components are preferably oxygen, nitrogen, carbon dioxide, noble gases, hydrogen, and/or alkanes.

It is preferable that the reaction takes place during addition of the α,β-unsaturated carboxylic acid derivative at a pressure of from 1 to 50 bar, preferably from 1 to 20 bar.

It is preferable that during the reaction of component C with components D or E the reaction solution is subject to an intensity of mixing corresponding to a rotational Reynolds number of from 1 to 1 000 000, preferably from 100 to 100 000.

It is preferable that olefin, α,β-unsaturated carboxylic acids, free-radical initiator, solvent, and hypophosphorous acid, and/or salts thereof are intimately mixed with energy input of from 0.083 to 10 kW/m$^3$, preferably from 0.33 to 1.65 kW/m$^3$.

Preferred apparatuses are stirred tanks, stirred-tank cascades, flow tubes, bubble columns, and scrubbers.

It is preferable that gaseous olefin components are introduced via nozzles (e.g. venturi nozzles), gassing stirrers, turbine stirrers, disk stirrers.

The invention also provides the use of the low-halogen-content monocarboxy-functionalized dialkylphosphinic acid in its form of the abovementioned mixtures as flame retardant or as intermediate for preparation of flame retardants. The invention also provides flame retardants which comprise low-halogen-content monocarboxy-functionalized dialkylphosphinic acids in their form of the abovementioned mixtures.

Preferred additives for the inventive stabilized flame retardants are antioxidants such as aromatic amines, sterically hindered phenols (butylated hydroxytoluene (BHT)), thiobisphenol, relatively high-molecular-weight polyphenols, tetrakis(methylene[2,5-di-tert-butyl-4-hydroxyhydrocinnamate])methane (Irganox 1010), octadecyl 3,5-di-tert-butyl-4-hydroxyhydrocinnamate (Irganox 1076), organophosphites (tris(nonylphenyl)phosphite (TNPP)), thioesters (distearyl 3,3'-thiodipropionates, ditridecyl 3,3'-thiodipropionate, dilauryl 3,3'-thiodipropionate), metal deactivators (Irganox 1024), vitamin E (alpha-tocopherol), lactone, hydroxylamine.

Preferred additives for the inventive stabilized flame retardants are antistatic agents, such as fatty acid esters (glycerol, polyethylene glycol esters, sorbitol esters), quaternary ammonium compounds, ethoxylated amines, alkylsulfonates.

Preferred additives for the inventive stabilized flame retardants are blowing agents such as azodicarbonamide, p,p-oxybis(benzenesulfonyl hydrazide) (OBSH), 5-phenyltetrazole (5PT), p-toluenesulfonylsemicarbazide (TSSC), trihydrazinotriazine (THT).

Preferred additives for the inventive stabilized flame retardants are flame retardants such as alumina trihydrate, antimony oxide, brominated aromatic or cycloaliphatic hydrocarbons, phenols, ethers, chloroparaffin, hexachlorocyclopentadiene adducts (Dechloran Plus, Occidental Chemical Co), red phosphorus, melamine derivatives, melamine cyanurates, ammonium polyphosphates, magnesium hydroxide.

Preferred additives for the inventive stabilized flame retardants are heat stabilizers such as lead stabilizers, (dibasic lead phthalate, dibasic lead stearate, lead silicate, monobasic and tribasic lead sulfate, dibasic lead carbonate, dibasic lead phosphite), mixed metal salts (barium cadmium salts of, and barium zinc salts and calcium zinc salts of, 2-ethylhexylcarboxylic acid), stearic acid, ricinoleic acid, and/or lauric acid and, respectively, substituted phenols, organotin stabilizers (mono- and dialkyltin mercaptides, (thioglycolates), dialkyltin carboxylates (maleates, laurates, tin esters)), secondary heat stabilizers (alkyl/aryl organophosphites, epoxy compounds of unsaturated fatty acids, and esters of fatty acids).

Preferred additives for the inventive stabilized flame retardants are impact modifiers/processing auxiliaries such as acrylates, acrylonitrile-butadiene-styrene (ABS), chlorinated polyethylene (CPE), ethylene-propylene terpolymer (EPT), ethylene-vinyl acetate (EVA), methacrylate-butadiene-styrene (MBS).

Preferred additives for the inventive stabilized flame retardants are lubricants such as fatty acid amides (fatty acid monoamides, fatty acid bisamides, oleamides, erucamides, ethylenebisstearamide (EBSA), ethylenebisoleamide (EBOA)), fatty acid/esters of fatty acids ($C_{16}$-$C_{18}$ (palmitic acid, stearic acid, oleic acid)), fatty acid alcohols (cetyl alcohol, stearyl alcohol), waxes (paraffin waxes, polyethylene waxes), metal stearates (calcium stearate, zinc stearate, magnesium stearate, barium stearate, aluminum stearate, cadmium stearate, lead stearate). Preferred additives for the inventive stabilized flame retardants are light stabilizers such as UV absorbers (alkyl-substituted hydroxybenzophenones e.g. 2-hydroxy-4-alkoxybenzophenones, alkyl-substituted hydroxybenzothiazoles e.g. 2-hydroxy-3,5-dialkylbenzotriazoles), UV quenchers (nickel diethyldithiocarbamate and zinc diethyldithiocarbamate, n-butylaminenickel 2,2'-thiobis (4-tert-octylphenolate), nickel bis(monoethyl 3,5-di-tert-butyl-4-hydroxybenzyl)phosphonate), free-radical inhibitors (bis(2,2',6,6'-tetramethyl-4-piperidyl)sebacate (HALS)), agents that decompose hydroperoxide(dithiophosphates).

Further preference is given to antidrip agents, compatibilizers, fillers, reinforcing materials, nucleating agents, additives for laser marking, hydrolysis stabilizers, chain extenders, color pigments, and plasticizers.

The invention in particular provides the use of the inventive monocarboxy-functionalized dialkylphosphinic acids as flame retardant or as intermediate for preparation of flame retardants, for thermoplastic polymers such as polyesters, polystyrene, or polyamide, and for thermoset polymers such as unsaturated polyester resins, epoxy resins, polyurethanes, or acrylates.

Suitable polyesters derive from dicarboxylic acids and from dialcohols and/or from hydroxycarboxylic acids or from the corresponding lactones.

It is preferable that the dicarboxylic acid components or their esters used comprise terephthalic acid, isophthalic acid, 5-sulfoisophthalic acid, 5-sulfopropoxyisophthalic acid, naphthalene-2,6-dicarboxylic acid, diphenyl-p,p'-dicarboxylic acid, diphenoxyalkanedicarboxylic acids, trans-hexahydroterephthalic acid, adipic acid, sebacic acid, or 1,2-cyclobutanedicarboxylic acid. It is particularly preferable to use terephthalic acid.

It is particularly preferable to use terephthalic acid as main component.

It is preferable that the entirety of the dicarboxylic acid co-components amounts to at most 10 mol % of the entire dicarboxylic acid component.

It is preferable that the diol component is used in pure form or as co-component to another diol.

It is preferable that the diol components used comprise ethylene glycol, propane-1,3-diol, butane-1,3-diol, and the higher homologs of butane-1,3-diols, 2,2-dimethylpropane-1,3-diol, or 1,4-cyclohexanedimethanol, particularly preferably ethylene glycol. It is preferable that ethylene glycol is used as main component. It is preferable that the entirety of the diol co-components amounts to at most 10 mol % of the entire diol component.

Suitable polyesters are polyethylene terephthalate, polybutylene terephthalate (Celanex 2500, Celanex 2002, Celanese; Ultradur, BASF), poly-1,4-dimethylolcyclohexane terephthalate, polyhydroxybenzoates, and also block polyetheresters which derive from polyethers having hydroxy end groups; and polyesters modified with polycarbonates or modified with MBS.

Synthetic linear polyesters with permanent flame retarding are composed of dicarboxylic acid components, of diol components of the inventive low-halogen-content monocarboxy-functionalized dialkylphosphinic acid or of the monocarboxy-functionalized dialkylphosphinic acid prepared by the inventive process, as phosphorus-containing chain members. The phosphorus-containing chain members make up from 2 to 20% of the dicarboxylic acid content of the polyester. The resultant phosphorus content in the polyester is preferably from 0.1 to 5%, particularly preferably from 0.5 to 3%.

It is preferable to carry out direct esterification starting from the free dicarboxylic acid and diols, with subsequent polycondensation. It is preferable to begin by carrying out transesterification starting from dicarboxylic esters, in particular dimethyl esters, and then to carry out polycondensation using the catalysts conventionally used for this purpose.

During preparation of the polyester, the following can preferably also be added, beside the familiar catalysts: conventional additives (crosslinking agents, matting agents and stabilizers, nucleating agents, dyes and fillers, etc.).

It is preferable that the inventive low-halogen-content monocarboxy-functionalized dialkylphosphinic acid or the monocarboxy-functionalized dialkylphosphinic acid prepared by the inventive process is added prior to, during, or shortly prior to the end of, the polycondensation reaction.

It is preferable that the esterification takes place at temperatures of from 100 to 300° C., particularly from 150 to 250° C.

It is preferable that the polycondensation reaction is carried out at pressures of from 0.1 to 1.5 mbar and at temperatures of from 150 to 450° C., particularly from 200 to 300° C.

It is preferable that the flame-retardant polyester molding compositions prepared according to the invention are used in polyester moldings.

Preferred polyester moldings are filaments, fibers, foils, and moldings, comprising mainly terephthalic acid as dicarboxylic acid component and mainly ethylene glycol as diol component.

Preferred process for production of filaments and fibers is spinning, drawing, and post-treatment. Preferred processes for production of foils are extrusion, pressing, and injection molding.

It is preferable that the phosphorus content in filaments and fibers produced from flame-retardant polyester is from 0.1 to 18%, preferably from 0.5 to 15%.

It is preferable that the phosphorus content in foils produced from flame-retardant polyester is from 0.2 to 15%, preferably from 0.9 to 12%.

The inventively flame-retardant polyester filaments can preferably be used in single-component filaments or else as one component in bicomponent filaments together with other polymers.

Suitable polystyrenes are polystyrene, poly(p-methylstyrene), and/or poly(alpha-methylstyrene).

It is preferable that the suitable polystyrenes are copolymers of styrene or alpha-methylstyrene with dienes or with acrylic derivatives, e.g. styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methyl acrylate; or a mixture of high impact resistance composed of styrene copolymers and of another polymer, e.g. of a polyacrylate, of a diene polymer, or of an ethylene-propylene-diene terpolymer; or else block copolymers of styrene, e.g. styrene-butadiene-styrene, styrene-isoprene-styrene, styrene-ethylene/butylene-styrene, or styrene-ethylene/propylene-styrene.

It is preferable that the suitable polystyrenes are graft copolymers of styrene or alpha-methylstyrene, e.g. styrene on polybutadiene, styrene on polybutadiene-styrene copolymers or on polybutadiene-acrylonitrile copolymers, styrene and acrylonitrile (and, respectively, methacrylonitrile) on polybutadiene; styrene, acrylonitrile, and methyl methacrylate on polybutadiene; styrene and maleic anhydride on polybutadiene; styrene, acrylonitrile, and maleic anhydride or maleimide on polybutadiene; styrene and maleimide on polybutadiene, styrene and alkyl acrylates, respectively, alkyl methacrylates on polybutadiene, styrene and acrylonitrile on ethylene-propylene-diene terpolymers, styrene and acrylonitrile on polyalkyl acrylates or on polyalkyl methacrylates, styrene and acrylonitrile on acrylate-butadiene copolymers, or else a mixture of these, e.g. those known as ABS polymers, MBS polymers, ASA polymers, or AES polymers.

It is preferable that the polymers are polyamides and copolyamides which derive from diamines and from dicarboxylic acids, and/or from aminocarboxylic acids or from the corresponding lactams, examples being nylon-2,12, nylon-4 (poly-4-aminobutyric acid, ®Nylon 4, DuPont), nylon-4,6 (poly(tetramethyleneadipamide), poly(tetramethyleneadipic diamide), ®Nylon 4/6, DuPont), nylon-6 (polycaprolactam, poly-6-aminohexanoic acid, ®Nylon 6, DuPont, ®Akulon K122, DSM; ®Zytel 7301, DuPont; ®Durethan B 29, Bayer), nylon-6,6 (poly(N,N'-hexamethyleneadipic diamide), ®Nylon 6/6, DuPont, ®Zytel 101, DuPont; ®Durethan A30, ®Durethan AKV, ®Durethan AM, Bayer; ®Ultramid A3, BASF), nylon-6,9 (poly(hexamethylenenonane diamide), ®Nylon 6/9, DuPont), nylon-6,10 (poly(hexamethylenesebacamide), ®Nylon 6/10, DuPont), nylon-6,12 (poly(hexamethylenedodecanediamide), ®Nylon 6/12, DuPont), nylon-6/6,6 (poly(hexamethyleneadipamide-co-caprolactam), ®Nylon 6/66, DuPont), nylon-7 (poly-7-aminoheptanoic acid, ®Nylon 7, DuPont), nylon-7,7 (polyheptamethylenepimelamide, ®Nylon 7,7, DuPont), nylon-8 (poly-8-aminooctanoic acid, ®Nylon 8, DuPont), nylon-8,8 (polyoctamethylenesuberamide, ®Nylon 8,8, DuPont), nylon-9 (poly-9-aminononanoic acid, ®Nylon 9, DuPont), nylon-9,9 (polynonamethyleneazelamide, ®Nylon 9,9, DuPont), nylon-10 (poly-10-amino-decanoic acid, ®Nylon 10, DuPont), nylon-10,9 (poly(decamethyleneazelamide), ®Nylon 10,9, DuPont), nylon-10,10 (polydecamethylenesebacamide, ®Nylon 10,10, DuPont), nylon-11 (poly-11-aminoundecanoic acid, ®Nylon 11, DuPont), nylon-12 (polylaurolactam, ®Nylon 12, DuPont, ®Grillamid L20, Ems Chemie), aromatic polyamides derived from m-xylene, diamine, and adipic acid; polyamides prepared from hexamethylenediamine and iso- and/or terephthalic acid (polyhexamethyleneisophthalamide polyhexamethyleneterephthalamide) and, if appropriate, from an elastomer as modifier, e.g. poly-2,4,4-trimethylhexamethyleneterephthalamide or poly-m-phenyleneisophthalamide. Block copolymers of the abovementioned polyamides with polyolefins, with olefin copolymers, with ionomers, or with chemically bonded or grafted elastomers; or with polyethers, e.g. with polyethylene glycol, polypropylene glycol, or polytetramethylene glycol. Also EPDM- or ABS-modified polyamides or copolyamides; and also polyamides condensed during processing ("RIM polyamide systems").

The inventive monocarboxy-functionalized dialkylphosphinic acids are preferably used in molding compositions which are further used to produce polymer moldings. Preferred process for production of polymer moldings is injection molding.

The invention is illustrated in non-limiting fashion by the examples below.

EXAMPLE 1

Comparison with the Prior Art 470 g of ethyldichlorophosphane were used in the first step to synthesize this cyclic anhydride of 3-(ethylhydroxyphosphinyl)propionic acid (chlorine content 327 ppm) according to the prior art (V. K. Chajrullin, R. R. Shagidullin, Z. Obschei. Khim. 36 (1966), pp. 289-296). Repeated rectification using a packed column (Raschig rings) reduced chlorine content to 152 ppm. The distillate was then hydrolyzed with iced water. Excess water was removed by distillation and the 3-(ethylhydroxyphosphinyl)propionic acid produced was recrystallized from acetone. This gave 220 g (37% of theory) of 3-(ethylhydroxyphosphinyl)propionic acid whose chlorine content was 120 ppm.

EXAMPLE 2

636 g (6 mol) of sodium hypophosphite monohydrate dissolved in 860 g of water in a pressure reactor (glass autoclave) were used as initial charge. 432 g (6 mol) of acrylic acid and 73.4 g of a 7% strength hydrogen peroxide solution (2.5 mol %, based on acrylic acid) were added dropwise at from 65 to 80° C. at atmospheric pressure over a period of 2 h, from different vessels. Ethylene was then introduced into the reactor at from 80 to 105° C. by way of a reducing valve adjusted to 3 bar, until saturation had been achieved. 73.4 g of a 7% strength hydrogen peroxide solution (2.5 mol %, based on ethylene) were fed uniformly over a period of 6 h, with constant stirring (energy input of 0.8 kW/m$^3$), at ethylene pressure of from 2.5 to 2.9 bar and temperature of from 80 to 105° C.

After depressurization, the aqueous solution was acidified with about 5 g of concentrated sulfuric acid and water was removed by distillation in vacuo. Tetrahydrofuran was used to take up and extract the residue. The insoluble salts were removed by filtration. The solvent of the filtrate was removed in vacuo and the residue was recrystallized from acetone. This gave 732 g (74% of theory) of 3-(ethylhydroxyphosphinyl)propionic acid as colorless solid; chlorine content: <0.1 ppm.

EXAMPLE 3

Using the method of Example 2, 516 g (6 mol) of crotonic acid were first admixed, at from 75 to 90° C. in the presence of 73.4 g of a 7% strength hydrogen peroxide solution, with 636 g (6 mol) of sodium hypophosphite monohydrate dissolved in 860 g of water. The resultant reaction mixture was then reacted with ethylene in the presence of 73.4 g of a 7% strength hydrogen peroxide solution. Appropriate work-up gave 623 g (58% of theory) of 3-(ethylhydroxyphosphinyl) butyric acid as colorless solid; chlorine content: <0.1 ppm.

EXAMPLE 4

Using the method of Example 2, 432 g (6 mol) of acrylic acid were first admixed, at from 65 to 80° C. in the presence of 428 g of a 5% strength sodium peroxodisulfate solution (1.5 mol % based on acrylic acid) with 636 g (6 mol) of sodium hypophosphite monohydrate dissolved in 860 g of water. The resultant reaction mixture was then reacted with propylene in the presence of 428 g of a 5% strength sodium peroxodisulfate solution (1.5 mol % based on propylene). Appropriate work-up gave 655 g (61% of theory) of 3-(propylhydroxyphosphinyl)propionic acid as colorless solid; chlorine content: <0.1 ppm.

EXAMPLE 5

A mixture of 792 g of a 50% strength aqueous solution of hypophosphorous acid (6 mol) and 300 g of acetic acid was used as initial charge in a pressure reactor (glass autoclave). Once the reaction mixture had been heated to 115° C., butylene was introduced into the reactor by way of a reducing valve adjusted to 3 bar until saturation had been achieved. 51.6 g of a 5% strength solution (0.26 mol %, based on butylene) of azoisobutyronitrile AIBN acidified with acetic acid were fed uniformly over a period of 6 h, with continuous stirring, at butylene pressure of from 2.5 to 2.9 bar and temperature of from 125 to 145° C. After depressurization, 432 g (6 mol) of acrylic acid and 51.6 g of a 5% strength AIBN solution (0.26 mol %, based on acrylic acid) acidified with acetic acid were added dropwise at from 90 to 100° C. at atmospheric pressure within a period of 3 h, from different feed vessels.

The solvent composed of water and acetic acid was then removed by distillation in vacuo, the residue was recrystallized from acetone/dioxane (3:1). This gave 695 g (60% of theory) of 3-(butylhydroxyphosphinyl)propionic acid as colorless solid; chlorine content: <0.1 ppm.

EXAMPLE 6

636 g (6 mol) of sodium hypophosphite monohydrate dissolved in 860 g of water were used as initial charge in a pressure reactor (glass autoclave). Once the reaction mixture had been heated to 100° C., ethylene was introduced into the reactor by way of a reducing valve adjusted to 3 bar, until saturation had been achieved. A solution of 428.4 g of a 5% strength sodium peroxodisulfate solution (1.5 mol %, based on ethylene) was fed uniformly over a period of 4 h, with constant stirring, at ethylene pressure of from 2.5 to 2.9 bar and temperature of from 100 to 130° C. After depressurization, 602 g (7 mol) of methacrylic acid and 500 g of a 5% strength sodium peroxodisulfate solution (1.5 mol %, based on methacrylic acid) were added dropwise within a period of 1 h at from 90 to 100° C. at atmospheric pressure, from different feed vessels.

The aqueous solution was then acidified with about 5 g of concentrated sulfuric acid and water was removed by distillation in vacuo. Tetrahydrofuran was used to take up and extract the residue. The insoluble salts were removed by filtration. The solvent of the filtrate was removed in vacuo and the residue was recrystallized from acetone. This gave 591 g (55% of theory) of 3-(ethylhydroxyphosphinyl)-2-methylpropionic acid as colorless solid; chlorine content: <0.1 ppm.

EXAMPLE 7

Using the method of Example 6, 636 g (6 mol) of sodium hypophosphite monohydrate dissolved in 860 g of water were first ethylated in the presence of 428 g of a 5% strength sodium peroxodisulfate solution (1.5 mol %, based on ethylene), and 700.8 g (7 mol) of tiglic acid were then admixed with this mixture in the presence of 500 g of a 5% strength sodium peroxodisulfate solution (1.5 mol %, based on tiglic acid). Appropriate work-up gave 579 g (50% of theory) of 3-(ethylhydroxyphosphinyl)-2-methylbutyric acid as colorless solid; chlorine content: <0.1 ppm.

EXAMPLE 8

636 g (6 mol) of sodium hypophosphite monohydrate dissolved in 860 g of water were used as initial charge in a pressure reactor (glass autoclave). Once the reaction mixture had been heated to 120° C., 1-hexene was introduced into the reactor by way of a reducing valve adjusted to 3 bar, until saturation had been achieved. 142.8 g of 5% strength sodium peroxodisulfate solution (1.5 mol %, based on 1-hexene) were fed uniformly over a period of 1 h, with constant stirring (energy input of 1.1 kW/m³) at hexene pressure of from 2.5 to 2.9 bar and temperature of from 120 to 140° C. After depressurization, 432 g (6 mol) of acrylic acid and 428 g of a 5% strength sodium peroxodisulfate solution (1.5 mol %, based on acrylic acid) were added dropwise at from 90 to 100° C. at atmospheric pressure within a period of 2 h, from different feed vessels. Once the reaction mixture had been heated to 120° C., 1-hexene was again introduced into the reactor by way of a reducing valve adjusted to 3 bar, until saturation had been achieved. 428 g of a 5% strength sodium peroxodisulfate solution (1.5 mol %, based on 1-hexene) were fed uniformly over a period of 6 h, with constant stirring, at hexene pressure of from 2.5 to 2.9 bar and temperature of from 120 to 140° C.

The aqueous solution was then acidified with about 5 g of concentrated sulfuric acid, and water was removed by distillation in vacuo. Tetrahydrofuran was used to take up and extract the residue. The insoluble salts were removed by filtration. The solvent of the filtrate was removed in vacuo and the residue was recrystallized from amyl alcohol/acetone (2:1). This gave 769 g (60% of theory) of 3-(hexylhydroxyphosphinyl)propionic acid as colorless solid; chlorine content: <0.1 ppm.

EXAMPLE 9

By analogy with Example 8, 636 g (6 mol) of sodium hypophosphite monohydrate and 15 g of concentrated sulfuric acid were dissolved in 860 g of water. The mixture was first reacted with propylene within a period of 2 h in the presence of 214 g of a 5% strength sodium peroxodisulfate solution (1.5 mol %, based on propylene). 516.5 g (6 mol) of methyl acrylate were then admixed with this mixture in the presence of 428 g of a 5% strength sodium peroxodisulfate solution (1.5 mol %, based on methyl acrylate), and then propylene was again added in the presence of 214 g of a 5% strength sodium peroxodisulfate solution.

The resultant aqueous solution was acidified with about 5 g of concentrated sulfuric acid, and the water was removed by distillation in vacuo. Tetrahydrofuran was used to take up and extract the residue. The insoluble salts were removed by filtration, and the solvent of the filtrate was removed in vacuo. For hydrolysis of the ester, the residue was heated to 150° C. and then 450 g (25 mol) of water were added dropwise within a period of 3 h. The water and volatile constituents were then removed in vacuo, and the residue was recrystallized from acetone/dioxane (4:1). This gave 634 g (59% of theory) of 3-(propylhydroxyphosphinyl)propionic acid as colorless solid; chlorine content: <0.1 ppm.

EXAMPLE 10

636 g (6 mol) of sodium hypophosphite monohydrate dissolved in 860 g of water were used as initial charge in a pressure reactor (glass autoclave). Once the reaction mixture had been heated to 100° C., ethylene was introduced into the reactor by way of a reducing valve adjusted to 3 bar, until saturation had been achieved. 428.4 g of a 5% strength sodium peroxodisulfate solution (1.5 mol %, based on ethylene) were fed uniformly over a period of 4 h, with constant stirring, at ethylene pressure of from 2.5 to 2.9 bar and temperature of from 100 to 130° C. After depressurization, 216 g (3 mol) of acrylic acid and 214.2 g of a 5% strength sodium peroxodisulfate solution (1.5 mol, based on acrylic acid) were added dropwise at from 90 to 100° C. at atmospheric pressure within a period of 1 h, from different feed vessels.

The two steps were repeated at appropriate temperatures by again adjusting to an ethylene pressure of from 2.5 to 2.9 bar and then metering 214.2 g of a 5% strength sodium peroxodisulfate solution over a period of 2 h. 216 g (3 mol) of acrylic acid were then again admixed with the reaction mixture in the presence of 214.2 g of a 5% strength sodium peroxodisulfate solution.

The aqueous solution was then acidified with about 5 g of concentrated sulfuric acid and water was removed by distillation in vacuo. Tetrahydrofuran was used to take up and extract the residue. The insoluble salts were removed by filtration. The solvent of the filtrate was removed in vacuo and the residue was recrystallized from acetone. This gave 752 g (76% of theory) of 3-(ethylhydroxyphosphinyl)propionic acid as colorless solid; chlorine content: <0.1 ppm.

EXAMPLE 11

636 g (6 mol) of sodium hypophosphite monohydrate and 15 g of concentrated sulfuric acid dissolved in 860 g of water were used as initial charge in a pressure reactor (glass autoclave). 216 g (3 mol) of acrylic acid and 36.5 g of a 7% strength hydrogen peroxide solution (2.5 mol %, based on acrylic acid) were then added dropwise at from 75 to 90° C. at atmospheric pressure within a period of 1 h, from different feed vessels. Ethylene was then introduced into the reactor at from 80 to 105° C. by way of a reducing valve adjusted to 3 bar, until saturation had been achieved. 73 g of a 7% strength hydrogen peroxide solution (2.5 mol %, based on ethylene) were fed uniformly over a period of 4 h, with constant stirring, at ethylene pressure of from 2.5 to 2.9 bar and temperature of from 80 to 105° C. After depressurization, 216 g (3 mol) of acrylic acid and 36.5 g of a 7% strength hydrogen peroxide solution (2.5 mol %, based on acrylic acid) were again added dropwise within a period of 1 h at from 75 to 90° C., from different feed vessels. Water was then removed by distillation in vacuo. Tetrahydrofuran was used to take up and extract the residue. The insoluble salts were removed by filtration. The solvent of the filtrate was removed in vacuo and the residue was recrystallized from acetone. This gave 772 g (78% of theory) of 3-(ethylhydroxyphosphinyl)propionic acid as colorless solid; chlorine content: <0.1 ppm.

EXAMPLE 12

A mixture of 792 g of a 50% strength aqueous solution of hypophosphorous acid (6 mol) and 300 g of acetic acid was used as initial charge in a pressure reactor (glass autoclave). Once the reaction mixture had been heated to 115° C., ethylene was introduced into the reactor by way of a reducing valve adjusted to 3 bar, until saturation had been achieved. 49.3 g of 5% strength solution (0.5 mol %, based on ethylene) of azoisobutyronitrile AIBN acidified with acetic acid were fed uniformly over a period of 2 h, with constant stirring, at ethylene pressure of from 2.5 to 2.9 bar and temperature of from 120 to 140° C. After depressurization, 258.3 g (3 mol) of methyl acrylate and 49.3 g of a 5% strength solution (0.5 mol %, based on methyl acrylate) of AIBN acidified with acetic acid were added dropwise at from 90 to 110° C. at atmospheric pressure within a period of 1 h, from different feed vessels.

The following amounts were accordingly fed in alternation:
in the presence of ethylene, 29.6 g of 5% strength AIBN solution acidified with acetic acid,
155 g of methyl acrylate and 29.6 g of 5% strength AIBN solution acidified with acetic acid,
in the presence of ethylene, 19.7 g of 5% strength AIBN solution acidified with acetic acid,
103.3 g of methyl acrylate and 19.7 g of 5% strength AIBN solution acidified with acetic acid,
in the presence of ethylene, 29.6 g of 5% strength AIBN solution acidified with acetic acid.

The solvent composed of water and acetic acid was then removed by distillation in vacuo. For hydrolysis of the ester, the residue was heated to 150° C. and then 450 g (25 mol) of water was added dropwise within a period of 3 h. Water was then removed in vacuo and the residue was recrystallized from acetone. This gave 743 g (75% of theory) of 3-(ethylhydroxyphosphinyl)propionic acid as colorless solid; chlorine content: <0.1 ppm.

EXAMPLE 13

1. Ethylation 636 g (6 mol) of sodium hypophosphite monohydrate dissolved in 860 g of water were used as initial charge in a pressure reactor (glass autoclave). Once the reaction mixture had been heated to 100° C., ethylene was introduced into the reactor by way of a reducing valve adjusted to 3 bar, until saturation had been achieved. 428.4 g of a 5% strength sodium peroxodisulfate solution (1.5 mol %, based on ethylene) were fed uniformly over a period of 4 h, with constant stirring, at ethylene pressure of from 2.5 to 2.9 bar and temperature of from 100 to 130° C.

2. Esterification

The aqueous reaction solution was acidified with about 5 g of concentrated sulfuric acid and water was removed by distillation in vacuo. 700 g of butanol were used to take up and extract the residue. The insoluble salts were removed by filtration. A further 1530 g of butanol were admixed with the filtrate and the mixture was heated at atmospheric pressure under conditions giving water separation. Once esterification had ended, butanol was removed in vacuo and the residue was distilled by way of a Vigreux column in vacuo. This gave 586 g (65% of theory) of n-butyl ethanephosphonite as colorless liquid.

3. Acrylic Acid Addition Reaction 450 g (3 mol) of n-butyl ethanephosphonite obtained by the above process and 385 g (3 mol) of n-butyl acrylate were used as initial charge in a 1 l five-necked flask with thermometer, reflux condenser, high-performance stirrer, and dropping funnel. 15 ml of sodium butoxide (30%) were added dropwise, with stirring, at a rate such that the reaction temperature established was at most 120° C. The mixture was then heated for a further 20 min at 80° C., with stirring. The resultant crude product was distilled in vacuo. This gave 751 g (90% of theory) of butyl 3-(ethyl-n-butoxyphosphinyl)propionate as colorless liquid.

4. Hydrolysis 556 g (2 mol) of the resultant butyl 3-(ethyl-n-butoxyphosphinyl)propionate were used as initial charge in a 1 l five-necked flask with thermometer, reflux condenser, high-performance stirrer, and dropping funnel. 500 ml of water were metered in at 160° C. over a period of 4 h and a butanol/water mixture was removed by distillation. (The butanol removed by distillation was reused for esterification of the ethylphosphonous acid.) The solid residue was recrystallized from acetone. This gave 305 g (92% of theory) of 3-(ethylhydroxyphosphinyl)propionic acid as colorless solid; chlorine content: <0.1 ppm.

EXAMPLE 14

261 g (4.5 mol) of acetone and 588 g (3 mol) of 50% strength sulfuric acid were admixed with 792 g of a 50% strength aqueous solution of hypophosphorous acid (6 mol) and the reaction mixture was heated at reflux for 8 h. After cooling, the reaction mixture was neutralized with sodium hydroxide solution with cooling by ice, and the solvent was removed by distillation in vacuo. Ethanol was used to take up the residue and the insoluble salts were removed by filtration. The solvent of the filtrate was removed in vacuo. This gave 677 g (91% of theory) of 1-hydroxy-1-methylethylphosphinate.

EXAMPLE 15

744 g (6 mol) of 1-hydroxy-1-methylethylphosphinate dissolved in 840 ml of water were used as initial charge, and then 432 g (6 mol) of acrylic acid and 428 g of a 5% strength sodium peroxodisulfate solution (1.5 mol %, based on acrylic acid) were added dropwise within a period of 2.5 h at from 95 to 100° C. from different feed vessels. Water was then removed by distillation in vacuo. Acetone was eliminated thermolytically at from 120 to 160° C. in vacuo and collected in a cold trap. 800 ml of water was used to take up the bottom product. The reaction mixture was heated to 115° C. in a pressure reactor and then ethylene was introduced into the reactor by way of a reducing valve adjusted to 3 bar until saturation had been achieved. 428 g of a 5% strength sodium peroxodisulfate solution (1.5 mol %, based on ethylene) were fed uniformly over a period of 5 h, with constant stirring, at ethylene pressure of from 2.5 to 2.9 bar and temperature of from 100 to 115° C.

The aqueous solution was then acidified with about 5 g of concentrated sulfuric acid and water was removed by distillation in vacuo. Tetrahydrofuran was used to take up and extract the residue. The insoluble salts were removed by filtration. The solvent of the filtrate was removed in vacuo and the residue was recrystallized from acetone. This gave 717 g (72% of theory) of 3-(ethylhydroxyphosphinyl)propionic acid as colorless solid; chlorine content: <0.1 ppm.

EXAMPLE 16

Corrosion Test with Product from Example 1

The cyclic 3-(ethylhydroxyphosphinyl)propionic anhydride obtained from Example 1 prior to distillation was hydrolyzed with iced water. Water was removed by distillation and the residue was mixed with glycol in a ratio of 1:2 parts. Ablation via corrosion was 0.34 mm/a using 1.4571 steel at 230° C. in the full immersion test.

EXAMPLE 17

Corrosion Test with Product from Example 2

The 3-(ethylhydroxyphosphinyl)propionic acid obtained from Example 2 was mixed with glycol in a ratio of 1:2 parts. Ablation via corrosion was <0.01 mm/a using 1.4571 steel at 230° C. in the full immersion test.

This corrosion rate is considerably more advantageous than in Example 16. The corrosion test provides evidence of the suitability of the flame retardant for use during processing of flame retardants, of flame-retardant polymer molding compositions, and/or of flame-retardant polymer moldings.

The invention claimed is:
1. A process for preparation of a composition comprising:
A) from 98 to 100% by weight of at least one monocarboxy-functionalized dialkylphosphinic acid of the formula (I)

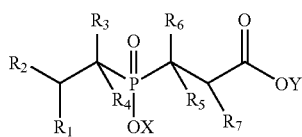

in which $R_1$, $R_2$, $R_3$, $R_4$, $R_5$, $R_6$, and $R_7$ are identical or different and, independently of one another, are H, methyl, ethyl, n-propyl, isopropyl, n-butyl, isobutyl, tert-butyl, or phenyl,
X and Y are identical or different and, independently of one another, are H, Li, Na, K, or $NH_4$, and B) from 0 to 2% by weight of at least one halogen, wherein the at least one halogen is a chemical compound in which atoms of the $7^{th}$ main group are present, chemically bonded to carbon or phosphorus, or are salts containing halide anions, where the entirety of the components always amounts to 100% by weight, comprising the steps of reacting component C, of the formula II

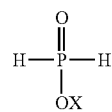

wherein X is H, Na, K, or $NH_4$ with a ketone to give 1-hydroxy-1-dialkylphosphinate, reacting the 1-hydroxy-1-dialkylphosphinate, in the presence of a free-radical initiator with component E of the formula IV

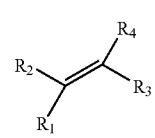

wherein $R_1$, $R_2$, $R_3$, and $R_4$ are defined as in formula I, removing the ketone, and reacting the resultant reaction mixture, in the presence of a free-radical initiator with component D, wherein component D is a α,β-unsaturated carboxylic acid of the formula III,

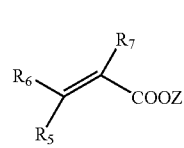

wherein $R_5$, $R_6$, and $R_7$ are defined as in formula I and Z is H, $C_{1-18}$-alkyl, or $C_{6-18}$-aryl, or is Y.

2. The process as claimed in 1, wherein the free radical initiator is selected from the group consisting of hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-tert-butyl peroxide, peroxodisulfuric acid, azodiisobutyronitrile, 2,2-azobis(2-amidinopropane) dihydrochloride 2,2'-azobis(N,N'-dimethyleneisobutyramidine) dihydrochloride and mixtures thereof.

3. The process as claimed in claim 1, wherein X is H and Z is H, methyl, ethyl, n-propyl, isopropyl, n-butyl, isobutyl, tert-butyl, hydroxyethyl, or hydroxypropyl.

4. The process as claimed in claim 1, wherein the free radical initiator is a free-radical, anionic, cationic, or photochemical initiator.

5. The process as claimed in claim 1, wherein the free radical initiator is a peroxide-forming compound, peroxo compound, an azo compound or a mixture thereof.

6. The process as claimed in claim 1, wherein the α,β-unsaturated carboxylic acid is acrylic acid, methyl acrylate, ethyl acrylate, methacrylic acid, hydroxyethyl acrylate, crotonic acid, ethyl crotonate, tiglic acid (trans-2,3-dimethylacrylic acid), (trans-)-2-pentenoic acid, furan-2-carboxylic acid, thiophene-2-carboxylic acid or a mixture thereof.

7. The process as claimed in claim 1, wherein the olefin is ethylene, propylene, n-butene, isobutene, 1-hexene, 1-heptene, 1-octene, styrene, α-methylstyrene or a mixture thereof.

8. The process as claimed in claim 1, wherein the reaction of component C with the ketone takes place at a temperature of from 50 to 150° C.

* * * * *